United States Patent [19]

LaHann et al.

[11] 4,424,205

[45] Jan. 3, 1984

[54] HYDROXYPHENYLACETAMIDES HAVING ANALGESIC AND ANTI-IRRITANT ACTIVITY

[75] Inventors: Thomas R. LaHann, Cleves, Ohio; Brian L. Buckwalter, Yardley, Pa.

[73] Assignee: The Procter & Gamble Company, Cincinnati, Ohio

[21] Appl. No.: 359,464

[22] Filed: Mar. 18, 1982

[51] Int. Cl.³ .................. C07C 103/76; A61K 7/155; A61K 31/165
[52] U.S. Cl. .................................... 424/72; 424/324; 564/170
[58] Field of Search ....................... 424/324; 564/170; 424/72

[56] References Cited

U.S. PATENT DOCUMENTS 3,268,582  8/1966  Zeile et al. ......................... 564/170
4,238,508 12/1980  Nelson ................................ 424/324
4,313,958  2/1982  LaHann ............................... 424/324

FOREIGN PATENT DOCUMENTS 626897  5/1963  Belgium .
56-39413 10/1981  Japan .
56-47752 11/1981  Japan .

OTHER PUBLICATIONS

Sohn, C. H. Boehringer Chemical Abstracts, (1964), #2861f.
Michalska, Zofia et al., Chemical Abstracts, vol. 77, (1972), #19271a.
Kiernan, "A Study of Chemically Induced Acute Inflammation in the Skin of the Rat" Quart. J. Exp. Physiol., vol. 62, (1977), pp. 151–161.
Jansco et al., "Direct Evidence for Neurogenic Inflammation and its Prevention by Denervation and by Pretreatment with Capsaicin," Br. J. Pharm. Chemother., vol. 31, (1967), pp. 138–151.
Arvier et al., "Modification by Capsaicin and Compound 40/80 of Dye Leakage Induced by Irritants in the Rat," Br. J. Pharm., vol. 59, (1977), p. 61–68.
Yaksh et al., "Intrathecal Capsaicin Depletes Substance P in the Rat Spinal Cord and Produces Prolonged Thermal Analgesia," Science, vol. 260, (1979), pp. 481–483.
Virus et al., "Pharmacologic Actions of Capsaicin: Apparent Involvement of Substance P and Serotonin," Life Sciences, vol. 24, (1979), pp. 1273–1281.
Jones et al., "The Relation Between Chemical Constitution and Pungency in Acid Amides," J. Chem. Soc., vol. 27, (1925), p. 2588–2598.
Newman, "Natural and Synthetic Pepper-Flavored Substances," Chem. Prod., (Mar. 1954), pp. 102–106.
Szolesanyi et al., "Sensory Effects of Capsaicin Congeners," Arzneim.-Forsch., vol. 25, (1975), pp. 1877–1881.
Szolesanyi et al., "Sensory Effects of Capsaicin Congeners," Arzneim.-Forsch., vol. 26, (1976), pp. 33–37.
Hegyes et al., "Synthesis of Homovanillic Acid Derivatives of Capsaicin-Like Effect," Acta. Phys. Chem., vol. 20, (1974), pp. 115–120.
T. Szeki, "Contributions Towards Understanding the Relation Between the Chemical Constitution and the Sharp Taste of Acylamines," Arch. Pharm., vol. 268, (1930), pp. 151–157.

Primary Examiner—Natalie Trousof
Assistant Examiner—L. Hendriksen
Attorney, Agent, or Firm—Steven J. Goldstein; Eric W. Guttag; Richard C. Witte

[57] ABSTRACT

A compound, or pharmaceutically acceptable salt thereof, having the formula:

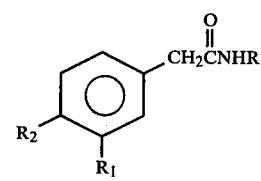

wherein R is a linear or branched $C_3$–$C_{11}$ alkyl, alkynyl or aralkyl group, a linear or branched $C_3$–$C_{22}$ alkenyl group, or an unbranched or branched $C_6$–$C_{11}$ cycloalkyl or cycloalkenyl group; and wherein one of $R_1$ and $R_2$ is OH, the other being OH or H. These hydroxyphenylacetamides have analgesic and/or anti-irritant activity when administered either topically or systemically.

23 Claims, No Drawings

HYDROXYPHENYLACETAMIDES HAVING ANALGESIC AND ANTI-IRRITANT ACTIVITY

TECHNICAL FIELD

The present invention relates to certain novel hydroxyphenylacetamides having analgesic and/or anti-irritant activity.

In general, analgesics fall into two broad categories. The simple analgesics, such as aspirin, are most effective against pain of integumental origin, headache, and muscle aches; the narcotics are more useful for deep or visceral pain. Narcotic analgesics such as morphine also produce more profound effects than simple analgesics, and are potentially addicting, with the development of tolerance and physical dependence. The narcotic analgesics appear to work through interaction with the endorphin/enkephalin system of the CNS; many of the simple, non-narcotic analgesics appear to work by inhibition of prostaglandin synthetase. The effect of narcotics is to elevate the pain threshold above the normal level; the non-narcotic analgesics typically act to raise an abnormally low pain threshold to the normal level. The narcotic analgesics are antagonized by N-allyl compounds such as naloxone; the non-narcotic analgesics are not.

In the field of anti-irritancy, dermal and tissue irritation can be caused by a number of different irritants such as acids and alkalis, keratolytics and proteolytics, depilatories, plant oils, and the like. In many instances, it is observed that compounds which effectively block the action of one class of irritants are totally or substantially ineffective with other classes of irritants. The problem in the art has been compounded by the inadequacy, or unavailability in some cases, of appropriate animal models of dermal irritation. For example, most laboratory animals are insensitive to poison ivy. As a consequence, the search has long continued, in a purely empirical way, for anti-irritant compositions—not always successfully.

It has been discovered that certain novel hydroxyphenylacetamides are analgesics and/or anti-irritants. With regard to analgesia, these compounds appear to be largely unrelated to the two known classes of analgesics. In certain tests, a number of these compounds produce a level of analgesia comparable to morphine, yet do not appear to involve the endorphin-enkephalin system, and thus should not be reversed by narcotic antagonists, such as naloxone. It is believed that these compounds will effectively prevent the development of cutaneous hyperalgesia. At high doses, it is believed that these compounds will also exert analgesic activity in standard models of deep pain, elevating the pain threshold above the normal value.

With regard to anti-irritancy, a number of these hydroxyphenylacetamides are active against several irritants, including croton oil and particularly depilatories (thioglycolates). These compounds appear to act, not as protectants or barriers, but, rather to block the irritation response. In addition, the hydroxyphenylacetamides of the present invention offer, in some instances, the benefit of reduced discomfort on application. By contrast, compounds such as capsaicin, which possess potent activity against certain irritants, can cause irritation and reddening when applied to the skin.

BACKGROUND ART

J. A. Kiernan, "A Study of Chronically Induced Acute Inflammation in the Skin of the Rat", *Quart. J. of Exp. Physiol.*, Vol. 62 (1977), pp. 151–161, states that capsaicin, N-(3-methoxy-4-hydroxybenzyl)-8-methyl-6-nonenamide, is known to confer resistance to certain chemical irritants.

Jancso, et al., "Direct Evidence for Neurogenic Inflammation and its Prevention by Denervation and by Pretreatment with Capsaicin", *Br. J. Pharmac. Chemother.*, Vol. 31, (1967), pp. 138–151, state that by repeated administration of capsaicin, ocular and/or cutaneous pain receptors can be desensitized to chemical, but not other, stimuli.

Arvier, et al., "Modification of Capsaicin and Compound 40/80 of Dye Leakage Induced by Irritants in the Rat", *Br. J. Pharm.*, Vol. 59, (1977) pp. 61–68, indicate that capsaicin reduces or blocks the edema formation associated with certain types of inflammation.

Yaksh et al., "Intrathecal Capsaicin Depletes Substance P in the Rat Spinal Cord and Produces Prolonged Thermal Analgesia", *Science*, Vol. 206, (1979), pp. 481–83, indicates that capsaicin is capable of producing prolonged thermal analgesia.

U.S. Pat. No. 4,238,508 to Nelson, issued Dec. 9, 1980, discloses that 3-hydroxyacetanilide provides analgesia for warm-blooded animals.

Belgian Pat. No. 626,897 to Corrodi et al., issued May 2, 1963, (Chem. Abs. 58:14442), discloses 3,4-dihydroxyphenylacetamides, including N-alkyl and N,N-dialkyl derivatives. Specific examples disclosed are 3,4-dihydroxyphenylacetamide, N-ethyl 3,4-dihydroxyphenylacetamide, and N,N-diethyl 3,4-dihydroxyphenylacetamide. These compounds are described as inhibiting certain enzymes, suppressing the dilation of bronchioles and potentiating the stimulation of the central nervous system.

Jones et al., "The Relation Between Chemical Constitution and Pungency in Acid Amides", *J. Chem. Soc.*, Vol. 27, (1925), pp. 2588–98, discloses that N-(3,4-dihydroxybenzyl)-nonamide, N-(4-hydroxybenzyl)-nonamide, N-(3,4-dihydroxybenzyl)-undecenamide, and N-(4-hydroxybenzyl)-undecenamide are pungent. Pungency increased on going from the 4-hydroxy to the 3,4-dihydroxybenzyl amides. See pp. 2590 and 2598. See also Newman, "Natural and Synthetic Pepper-Flavored Substances", (March, 1954), pp. 102–106, which lists the pungency of capsaicin-like analogs, including those amides disclosed in Jones et al., supra.

J. Szolesanyi et al., "Sensory Effects of Capsaicin Congeners", *Arzneim.-Forsch.*, Vol. 25, (1975), pp.1877–81, describes the pungency of various N-alkyl and N-cycloalkyl 3-methoxy-4-hydroxyphenylacetamides, including the N-isobutyl, N-octyl, N-dodecyl, N-cyclohexyl and N-cyclododecyl derivatives. Maximum pungency is disclosed as being reached at the N-octyl to the N-decyl derivatives. See also Szolesanyi et al., "Sensory Effects of Capsaicin Congeners", *Arzneim.-Forsch.*, Vol., 26, (1976), pp. 33–37 (chemically induced pain desensitizing potency of various N-alkyl and N-cycloalkyl 3-methoxy-4-hydroxyphenylacetamides described); Hegyes et al., "Synthesis of Homovanillic Acid Derivatives of Capsaicin-Like Effect", *Acta Phys. Chem.*, Vol. 20, (1974), pp. 115–20 (pungency and desensitizing ability of various N-alkyl and N-cycloalkyl 3-methoxy-4-hydroxyphenylacetamides described); French Pat. No. 1,336,388 to C. H. Boehringer Sohn., issued Aug. 30, 1963, (Chem. Abs. 58:2861) (preparation of N,N-dialkyl 3-methoxy-4-hydroxyphenylacetamides disclosed, including the N,N-dimethyl and diethyl derivatives).

Michalska et al., "Synthesis and Local Anesthetic Properties of N-substituted 3,4-Dimethoxyphenethylamine Derivatives", *Diss Pharm. Pharmacol.*, Vol. 24, (1972), pp. 17-25, (Chem. Abs. 77:19271a), discloses N-pentyl and N-hexyl 3,4-dimethoxyphenylacetamides which are reduced to the respective secondary amines. The secondary amines are disclosed as having local anesthetic properties. See also U.S. Pat. No. 3,268,582 to Zeile et al., issued Aug. 23, 1966, which discloses the preparation of N,N-dimethyl 3,4-dimethoxyphenylacetamide.

DISCLOSURE OF THE INVENTION

The present invention relates to analgesic and/or anti-irritant compounds, including pharmaceutically acceptable salts thereof, having the following formula:

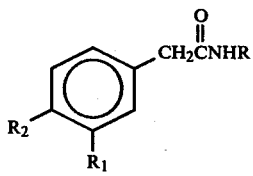

wherein R is a linear or branched $C_3$–$C_{11}$ (preferably $C_6$–$C_9$) alkyl, alkynyl or aralkyl group, a linear or branched $C_3$–$C_{22}$ (preferably $C_{12}$–$C_{18}$) alkenyl group, or an unbranched or branched $C_6$–$C_{11}$ cycloalkyl or cycloalkenyl group; and wherein one of $R_1$ and $R_2$ is OH, the other being OH or H. These compounds or salts thereof are hereafter generally referred to as hydroxyphenylacetamides. The 3,4-dihydroxyphenylacetamides have been found to have the highest analgesic activity with the n-octyl and n-nonyl derivatives being most preferred. The 3- or 4-hydroxyphenylacetamides have been found to have the best anti-irritant activity against thioglycolate depilatories with the n-octyl derivatives being most preferred.

The hydroxyphenylacetamides of the present invention can be readily prepared by the following general synthesis scheme.

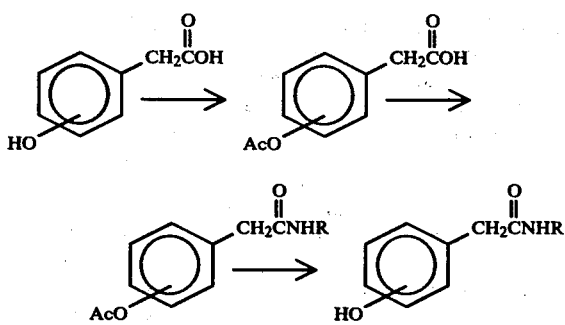

The mono- and dihydroxyphenylacetic acids are commercially available from several sources, and are readily acetylated.

DETAILED DESCRIPTION OF HYDROXYPHENYLACETAMIDES AND COMPOSITIONS CONTAINING SAME FOR PROVIDING ANALGESIA AND ANTI-IRRITANCY

A. Definitions

By "pharmaceutically acceptable salts" is meant those hydroxyphenylacetamide salts which are safe for topical or systemic administration. These salts include the sodium, potassium, calcium, magnesium, and ammonium salts.

By "safe and effective amount" is meant an amount of the hydroxyphenylacetamide effective to provide analgesia or anti-irritancy so as to alleviate or prevent the pain or irritation being treated at a reasonable benefit/risk ratio attendant with any medical treatment. The amount of the hydroxyphenylacetamide will vary with the particular condition being treated, the severity of the condition, the duration of the treatment, the specific formulation employed, the concentration of the hydroxyphenylacetamide therein, and like factors.

By "topical application" herein is meant the direct laying on or spreading of the hydroxyphenylacetamide or composition containing same on epidermal or epithelial tissue (including outer skin and oral, gingival, nasal, etc. tissue).

By "systemic administration" is meant the introduction of the hydroxyphenylacetamide or composition containing same into the tissues of the body, other than by topical application. Systemic administration thus includes, without limitation, intrathecal, epidural, intramuscular, intravenous, intraperitoneal, and subcutaneous administration.

By the term "comprise" as used herein is meant that various other inert ingredients, compatible drugs and medicaments, and steps can be employed in the compositions and methods of the present invention as long as the critical hydroxyphenylacetamides are present in the compositions and are used in the manner disclosed. The term "comprising" thus encompasses and includes the more restrictive terms "consisting essentially of" and "consisting of" which characterize the use of the essential hydroxyphenylacetamides in the compositions and methods disclosed herein.

By "compatible" herein is meant that the components of the composition are capable of being commingled without interacting in a manner which would substantially decrease the efficacy of the total composition under ordinary use situations.

All percentages herein are by weight of the composition unless otherwise specified.

B. Topical Compositions

The hydroxyphenylacetamides of the present invention are useful when topically applied to the skin. Compositions containing these hydroxyphenylacetamides are particularly useful for topical application. These compositions comprise a safe and effective amount, usually at least aout 0.5%, and preferably from about 1% to about 2% of the hydroxyphenylacetamide. The balance of the composition further comprises a pharmaceutically acceptable carrier. Suitable carriers for the hydroxyphenylacetamide preferably remain in place on the skin as a continuous film and resist being washed off easily by perspiration or by immersion in water. Generally, the carrier is organic in nature and capable of having dispersed or dissolved therein the hydroxyphenylacetamide. Lotions, creams, solutions, gels and solids are common physical forms of such compositions. A more detailed description of such forms follows.

1. Lotions

Suitable lotions comprise an effective amount of the hydroxyphenylacetamide; for about 1% to about 25%, preferably from about 3% to about 15%, of an emollient; the balance being water, a $C_2$ or $C_3$ alcohol, or a mixture of water and the alcohol. Numerous emollients are known. Examples of such emollients are as follows:

1. Hydrocarbon oils and waxes. Examples are mineral oil, petrolatum, paraffin, ceresin, ozokerite, microcrystalline wax, polyethylene, and perhydrosqualene.

2. Silicone oils, such as dimethylpolysiloxanes, methylphenylpolysiloxanes, water-soluble and alcohol-soluble silicone-glycol copolymers.

3. Triglyceride fats and oils such as those derived from vegetable, animal and marine sources. Examples include castor oil, safflower oil, cotton seed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl monostearate.

6. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.

8. Fatty acids having 9 to 22 carbon atoms. Suitable examples include pelargonic, lauric, myristic, palmitic, stearic, isostearic, hydroxystearic, oleic, linoleic, ricinoleic, arachidic, behenic, and erucic acids.

9. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

11. Ether-esters such as fatty acid esters of ethoxylated fatty alcohols.

12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated lanolin alcohols-esters, hydrogenolysates of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols 350, 550, 750, 2000, 5000, poly[ethylene oxide] homopolymers (M.W. 100,000–5,000,000), polyalkylene glycols and derivatives, hexylene glycol (2-methyl-2,4-pentadiol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivatives of trimethylolpropane are examples thereof.

14. Polyhydric alcohol esters. Ethylene glycol mono- and di-fatty acid esters, diethylene glycol mono- and di-fatty acid esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glycerol monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

15. Wax esters such as beeswax, spermaceti, myristyl myristate, stearyl stearate.

16. Beeswax derivatives, e.g. polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids such as lecithin and derivatives.

19. Sterols. Cholesterol, cholesterol fatty acid esters are examples thereof.

20. Amides such as fatty acid amides, ethoxylated fatty acid amides, solid fatty acid alkanolamides.

The lotions further comprise from about 1% to about 10%, preferably from about 2% to about 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan, and hydrophilic wax esters. Suitable anionic emulsifiers include the fatty acid soaps, e.g sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such as emollient, an additional emulsifier is not needed, though it can be included in the composition.

The balance of the lotion is water, a $C_2$ or $C_3$ alcohol, or a mixture of water and the alcohol. The lotions are formulated by simply admixing all of the components together. Preferably the hydroxyphenylacetamide is dissolved in the mixture. Optional components such as common additives can be included. One common additive is a thickening agent at a level from about 1% to about 10% of the composition. Examples of suitable thickening agents include: cross-linked carboxypolymethylene polymers, ethyl cellulose, polyethylene glycols, gum tragacanth, gum kharaya, xanthan gums and bentonite.

2. Creams

Suitable creams comprise an effective amount of the hydroxyphenylacetamide; from about 5% to about 50%, preferably about 10% to about 25% of an emollient; the balance being water. The emollients previously described for lotions are also used in creams. Optionally the cream form contains a suitable emulsifier, as previously described for lotions. When an emulsifier is included, it is in the cream at a level from about 3% to about 50%, preferably from about 5% to about 20%.

3. Solutions

Suitable solution forms comprise an effective amount of the hydroxyphenylacetamide, the balance being a suitable organic solvent. Suitable organic materials useful as the solvent or as part of the solvent system are propylene glycol, polyethylene glycol (M.W. 200–600), polypropylene glycol (M.W. 425–2025), glycerin, sorbitol esters, 1,2,6-hexanetriol, ethanol, isopropanol, diethyl tartrate, butanediol, and mixtures thereof. Such solvent systems can also contain water.

These compositions in solution form can be applied to the skin as is, or else can be formulated into an aerosol and applied to the skin as a spray-on. The aerosol compositions further comprise from about 25% to about 80%, preferably from about 30% to about 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Compositions herein can be formulated into a gel form by simply admixing a suitable thickening agent to the previously described solution compositions. Examples of suitable thickening agents have been previously described with respect to the lotions.

The gel compositions comprise an effective amount of the hydroxyphenylacetamide; from about 5% to about 75%, preferably from about 10% to about 50%, of an organic solvent as previously described; from about 0.5% to about 20%, preferably from about 1% to about 10%, of the thickening agent; the balance being water.

5. Solids

The compositions herein can also be formulated as a solid. Such forms have use as a stick-type composition intended for application to the lips or other parts of the body. Such compositions comprise an effective amount of the hydroxyphenylacetamide; and from about 50% to about 98%, preferably from about 60% to about 90%, of the previously described emollients. This composition can further comprise from about 1% to about 20%, preferably from about 5% to about 15%, of a suitable thickening agent, and optionally emulsifiers and water. Thickening agents previously described with respect to the gelled compositions are suitable herein.

Additives commonly found in topical compositions such as preservatives, e.g. methyl and ethyl-paraben, dyes and perfume can be included in any of the previously described compositions.

C. Pharmaceutical Compositions and Dosage Forms for Systemic Administration

The hydroxyphenylacetamides of the present invention are also useful when administered systemically, for example by parenteral administration. The dosage of the hydroxyphenylacetamide which is both safe and effective to provide analgesic or anti-irritant activity will vary with the particular condition being treated, the severity of the condition, the duration of treatment, the specific hydroxyphenylacetamide employed and its usage concentration, and like factors within the specific knowledge and expertise of the patient or the attending physician and commensurate with a reasonable benefit/risk ratio associated with the use of any drug. The systemic dosages and dosage ranges given herein are based on delivery of the hydroxyphenylacetamide to a 70 kg human and can be adjusted to provide equivalent dosages for patients of different body weights.

For mammals, especially humans, individual doses of from about 0.1 mg to about 100 mg with total dosages of from about 0.5 mg to about 500 mg are acceptable. Individual doses of from about 0.5 mg to about 50 mg with total dosages of from about 1 mg to about 100 mg are preferred. Individual doses of from about 5 mg to about 25 mg with total dosages of from about 10 mg to about 50 mg are especially preferred. While dosages higher than the foregoing are effective, toxicity and side effects will present problems in some individuals.

The hydroxyphenylacetamides can be administered parenterally in combination with a pharmaceutically acceptable carrier such as corn oil, Cremophor EL, or sterile, pyrogen-free water and a water-miscible solvent (e.g. ethyl alcohol) at a practical amount of the hydroxyphenylacetamide per dose. Parenteral administration can be by subcutaneous, intradermal, intramuscular, intraarticular, or intravenous injection. The dosage by these modes of administration is usually in the range of from about 10 mg to about 500 mg per day.

With regard to pharmaceutical compositions for systemic administration, the term "pharmaceutically acceptable carrier" denotes a solid or liquid filler, diluent, or encapsulating substance. Some examples of the substances which can serve as pharmaceutical carriers for the hydroxyphenylacetamides of the present invention include: sugars such as lactose, glucose and sucrose; starches such as corn starch and potato starch; cellulose and its derivatives, such as sodium carboxymethylcellulose, ethyl cellulose, cellulose acetate; powdered tragacanth; malt; gelatin; talc, stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; cocoa butter (suppository base), emulsifiers, such as the Tweens ® as well as other non-toxic compatible substances typically used in pharmaceutical formulations. Wetting agents and lubricants such as sodium lauryl sulfate, as well as coloring agents, flavoring agents and preservatives, can also be present.

The pharmaceutical carrier employed in conjunction with the hydroxyphenylacetamide is used at a concentration sufficient to provide a practical size to dosage relationship. Preferably, the pharmaceutical carrier comprises at least about 98% by weight of the total composition.

D. Methods for Providing Analgesia and Anti-irritancy

The present invention encompasses methods for providing analgesia or anti-irritancy in humans or lower animals in need thereof by administering to the human or lower animal a safe and effective amount, usually from about 10 mg to about 500 mg per patient per day, of a hydroxyphenylacetamide or composition containing same. The hydroxyphenylacetamide or composition containing same can be administered by topical application or systemic administration. The hydroxyphenylacetamides and compositions containing same can be used to treat and prevent pain and to provide analgesia in various disorders at the deeper structures, muscles, tendons, bursa and joints associated with disease and trauma, and in various other conditions in which compounds such as aspirin and morphine have heretofore been used to alleviate pain and discomfort.

A "stairstep" dose pattern of sequentially increasing doses is useful for intraperitoneal administration in overcoming temporary side effects and in administering larger doses of the hydroxyphenylacetamides of the present invention. Thus, the initial dose should be selected to provide minimal side effects, and subsequent doses should be increased until the desired level of activity is obtained while still minimizing side effects. In general, an initial dose of 2-10 mg/kg can be conveniently used, followed by doubling of each subsequent dose until the desired treatment dosage is reached. The doses are preferably separated by a period of at least about two hours.

E. Depilatory Compositions Having Reduced Dermal Irritation and Methods for Reducing or Preventing Irritation Caused by Depilatory Agents The present invention also encompasses depilatory compositions having reduced dermal irritation, which comprise: (a) a depilatory amount (e.g. at least about 2%) of a thioglycolate depilatory agent; and (b) a hydroxyphenylacetamide in an amount effective to reduce the dermal irritation caused by the thioglycolate depilatory agent. The depilatory compositions can be formulated using the pharmaceutically acceptable carriers previously described for topical compositions.

The present invention further encompasses a method for preventing or reducing the dermal irritation caused by a thioglycolate depilatory agent, which comprises the step of applying to at least a portion of a depilated area a hydroxyphenylacetamide (or composition containing same) in an amount effective to prevent or reduce the irritation caused by treatment of the depilated area with the thioglycolate depilatory agent.

By "thioglycolate depilatory agent" is meant thioglycolic acid, its alkali metal, alkaline earth metal, and ammonium salt(s), or mixtures of the acid and its salt(s).

By "an amount effective to prevent or reduce irritation" is meant an amount of the hydroxyphenylacetamide (or composition containing same) effective to reduce or prevent the irritation caused by treatment of the depilated area with the thioglycolate depilatory agent at a reasonable benefit/risk ratio. The amount of depilatory agent at a reasonable benefit/risk ratio. The amount of the hydroxyphenylacetamide used will vary with the severity of the irritation, the duration of the treatment, the specific formulation employed, the concentration of the hydroxyphenylacetamide therein, and like factors.

By "depilated area" is meant that area which is, or is about to be, depilated by treatment with a thioglycolate depilatory agent.

By the term "applying" with regard to preventing or reducing depilatory irritation is meant the direct laying on or spreading of the hydroxyphenylacetamide (including compositions containing same) on skin tissue which is, or is about to be depilated. The hydroxyphenylacetamide can be applied before and/or after treatment of the depilated area with the thioglycolate depilatory agent to prevent or reduce irritation caused thereby. Application of the hydroxyphenylacetamide to the depilated area after treatment with the depilatory agent is preferred, especially when lower concentrations of the hydroxyphenylacetamide are used. The number of applications needed to provide effective irritation prevention or reduction can depend upon the concentration of the hydroxyphenylacetamide used, and when the hydroxyphenylacetamide is applied in relation to the treatment with the depilatory agent. Application of the hydroxyphenylacetamide soon after depilation, e.g. within about 6 to about 12 hours, provides effective irritation prevention or reduction, especially in conjunction with additional applications on subsequent days. Multiple applications (2 or more sequential, time spaced applications) soon after depilation are particularly effective. The length of time during which the hydrophenylacetamide is left on the depilated area can also determine its effectiveness. An application duration of at least about 1 hour, preferably about 1 to about 2 hours, should provide effective irritation prevention or reduction.

SYNTHESIS OF SPECIFIC HYDROXYPHENYLACETAMIDES

A. 3,4-Dihydroxyphenylacetamides

Octyl 3,4-dihydroxyphenylacetamide was prepared by the following method:

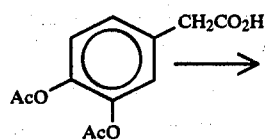

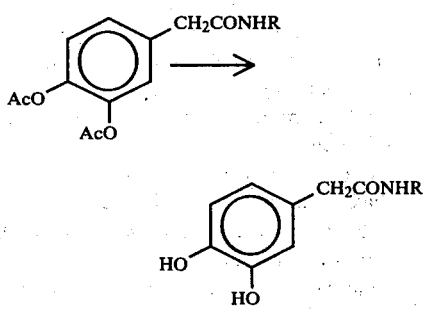

1. Octyl 3,4-diacetoxyphenylacetamide

A solution of 10 g 3,4-diacetoxyphenylacetic acid, 8 ml of thionyl chloride, and 15 ml of chloroform was refluxed for 2 hours. The solvent was removed on a rotary evaporator and the crude acid chloride used immediately. To an ice-cold solution of 3,4-diacetoxyphenylacetyl chloride and 100 ml of benzene was added dropwise a solution 10.75 g of octylamine and 40 ml of ether. The reaction mixture was stirred overnight at room temperature. The mixture was transferred to a separatory funnel and washed with 100 ml of 1 N HCl, twice with 100 ml of water and 100 ml brine. The ether phase was dried ($Na_2SO_4$), filtered, and evaporated to yield 16.88 g of a mixture containing octyl 3,4-diacetoxyphenylacetamide.

2. Octyl 3,4-dihydroxyphenylacetamide

To a chilled solution of 16.88 g of the mixture containing octyl 3,4-diacetoxyphenylacetamide and 100 ml of methanol was added 16 ml of 5 N NaOH. The reaction mixture was stirred for two hours at room temperature. The methanol was removed on a rotary evaporator, the residue dissolved in 100 ml of 0.1 N NaOH and the solution extracted with 100 ml of ether. The resulting aqueous phase was acidified with conc. HCl and thrice extracted with 150 ml of ether. The combined ether extracts were washed with 100 ml $H_2O$, dried ($Na_2SO_4$), filtered and evaporated to yield 8.91 g of crude product. This material was chromatographed on silica gel with 60% ethyl acetate/hexane and subsequently recrystallized from ether-pentane to yield 2.3 g of white crystalline octyl 3,4-dihydroxyphenylacetamide, mp. 83°–85° C. Anal. Calc'd for $C_{16}H_{25}NO_3$: C, 68.78; H, 9.02; N, 5.01. Found: C, 68.69; H, 9.08; N, 4.98.

The nonyl derivative was made in similar fashion:

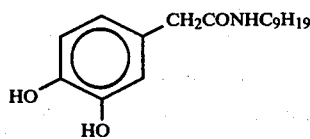

m.p. 77°–79° C.

Anal. Calcd for $C_{17}H_{27}NO_3$: C, 69.59; H, 9.28; N, 4.77. Found: C, 69.66; H, 9.30; N, 4.69.

B. 3- or 4-Hydroxyphenylacetamides

In similar manner was prepared octyl 3-hydroxyphenylacetamide:

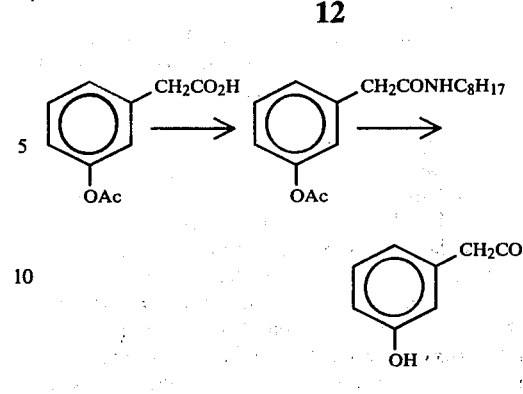

1. Octyl 3-acetoxyphenylacetamide

A solution of 6.36 g 3-acetoxyphenylacetic acid and 10 ml of thionyl chloride was refluxed for one hour. The solvent was removed on a rotary evaporator, 15 ml of dry benzene was added and re-evaporated to yield crude 3-acetoxyphenylacetyl chloride. To a cooled solution of the acid chloride in 35 ml benzene was added dropwise a solution 8.9 g of octyl amine and 10 ml of ether. The reaction mixture was stirred at room temperature for three hours, the solids filtered, and the filtrate transferred to a separatory funnel and extracted with 50 ml of 1 N HCl, 50 ml of $H_2O$ and 50 ml of brine. The resulting organic solution was dried ($MgSO_4$), filtered, and evaporated to yield 10.14 g of a mixture containing octyl 3-acetoxyphenylacetamide.

2. Octyl 3-hydroxyphenylacetamide

To a chilled solution of 10.14 g of the mixture containing octyl 3-acetoxyphenylacetamide and 100 ml of methanol was added 12.63 ml of 5 N NaOH. The mixture was stirred at room temperature for 3 hours after which the methanol was removed in vacuo. The residue was dissolved in 100 ml of 1 N NaOH and extracted with 50 ml of ether. The resulting aqueous phase was acidified with conc. hydrochloric acid and extracted twice with 100 ml of ether. The combined ether extracts were washed with 75 ml of water and 75 ml of brine, dried ($MgSO_4$), filtered, and evaporated to provide 7.55 g of crude product which was recrystallized from toluene-pentane to yield 5.03 g of octyl 3-hydroxyphenylacetamide, m.p. 60°–62° C. Anal. Calc'd for $C_{16}H_{25}NO_2$: C, 73.00; H, 9.58; N, 5.32. Found: C, 72.86; H, 9.63; N, 5.16.

In a similar manner, but starting with 4-acetoxyphenylacetic acid, was prepared:

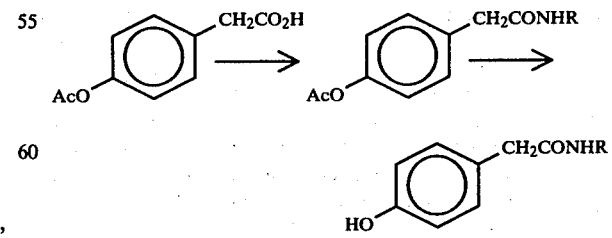

Octyl 4-hydroxyphenylacetamide: m.p. 86°–88° C.
Nonyl 4-hydroxyphenylacetamide: m.p. 93°–95° C.
Anal. Calc'd for $C_{17}H_{27}NO_2$: C, 73.60; H, 9.80; N, 5.04. Found: C, 73.80; H, 9.90; N, 5.03.

Decyl 4-hydroxyphenylacetamide: m.p. 94°–96° C. Anal. Calc'd for $C_{18}H_{29}NO_2$: C, 74.18; H, 10.03; N, 4.80. Found C, 74.30; H, 10.07; O, 4.74.

It can be seen that preparation of the desired hydroxyphenylacetamides of the present invention can be accomplished by selection of the appropriate starting materials, using the foregoing techniques, which are well within the skill of the synthetic chemist.

EFFECTIVENESS OF HYDROXYPHENYLACETAMIDES IN PRODUCING ANALGESIA AND IN REDUCING OR PREVENTING DEPILATORY IRRITATION

A. Analgesia

1. Mouse Hot Plate Tests

The Mouse Hot Plate (MHP) model system is designed to detect and evaluate agents which elevate the threshold for the perception of pain. Classically, this method has been utilized primarily to evaluate narcotic type analgesic agents such as morphine. Unless administered in toxic quantities, nonsteroidal anti-inflammatory agents such as aspirin or acetaminophen exhibit little or no activity in this system.

Male CF-1 mice were used. Animals were divided into groups of 8–10 and then tested on the "hot plate" to determine their predrug response times which ranged from 4.8 to 5.1 seconds (average). Each animal was then treated with either a test composition (0.5% to 10% of the particular hydroxyphenylacetamide in an isotonic saline solution containing ethyl alcohol and Tween 80, or in a solution containing ethyl alcohol and pyrrolidone) or a control composition (same as test composition but without the hydroxyphenylacetamide). Treatment was by injection prior to test initiation.

2. Procedure

The mice were placed on a 55° C. heated surface and their responses were observed. The endpoint was either a rapid fanning or licking of a paw. To prevent physical injury, the animals were not allowed to remain in contact with the heated surface for more than 60 seconds. The exposure time required to elicit the endpoint response is a measure of the pain threshold. The difference in time required to elicit the endpoint response before and after treatment provides a measure of analgesia. The increase in time required to elicit the endpoint response in treated animals versus the control composition is a second measure of analgesia.

3. Results a. 3,4-Dihydroxyphenylacetamides

The results from the MHP testing of the 3,4-dihydroxyphenylacetamides were as follows:

TABLE I

| Compound | Method** | Dosage (mg/kg)*** | Post-Drug Response (sec) |
|---|---|---|---|
| Aspirin* | O | 360 | 6.0 |
| Acetaminophen* | O | 450 | 5.3 |
| Morphine Sulfate* | IP | 13 | 13.1 |
| Morphine Sulfate* | IP | 25 | 17.4 |
| Control | SC or IP | — | 4.8–5.1 |
| Decyl | SC | 0.68 mM/kg | 4.8 |
| Decyl | SC | 1.25 mM/kg | 5.0 |
| Nonyl | SC | 1.25 mM/kg | 5.6 |
| Nonyl | IP | 4,8,15,25 | 12.7 |
| Nonyl | IP | 4,8,15,25,50,100 | 51.7 |
| Octyl | SC | 4,8,15,25,50 | 9.2 |
| Octyl | SC | 100 | 14.8 |

TABLE I-continued

| Compound | Method** | Dosage (mg/kg)*** | Post-Drug Response (sec) |
|---|---|---|---|
| Octyl | SC | 1.25 mM/kg | 15.1 |
| Octyl | SC | 1.25 mM/kg | >56.1 |
| Octyl | IP | 4,8,15,25 | 13.8 |
| Octyl | IP | 4,8,15,25 | >23.5 |
| Octyl | IP | 4,8,15,25,50 | 12.4 |
| Octyl | IP | 4,8,15,25,50 | Dead |

*Commercial Analgesics
**O = oral; SC = subcutaneous; IP = intraperitoneal
***Multiple doses were 2 hours apart The data from Table I shows that nonyl and octyl 3,4 dihydroxyphenylacetamide have significant analgesic activity relative to the control composition and to the commercial analgesics (aspirin, acetaminophen and morphine sulfate).

b. 4-Hydroxyphenylacetamides

The results from the MHP testing of the 4-hydroxyphenylacetamides were as follows:

TABLE II

| Compound | Method** | Dosage (mg/kg)*** | Post-Drug Response (sec.) |
|---|---|---|---|
| Aspirin* | O | 360 | 6.0 |
| Acetaminophen* | O | 450 | 5.3 |
| Morphine Sulfate* | IP | 13 | 13.1 |
| Morphine Sulfate* | IP | 25 | 17.4 |
| Control | SC or IP | — | 4.8–5.1 |
| Decyl | SC | 1.25 mM/kg | 6.9 |
| Decyl | IP | 4,8,15,25 | 7.0 |
| Decyl | IP | 4,8,15,25 | 6.7 |
| Decyl | IP | 4,8,15,25 | 5.8 |
| Decyl | IP | 4,8,15,25,50,100 | 5.5 |
| Nonyl | SC | 1.25 mM/kg | 7.3 |
| Nonyl | IP | 4,8,15,25 | 5.2 |
| Nonyl | IP | 4,8,15,25,50,100 | 6.3 |
| Nonyl | IP | 4,8,15,25,50,1,, | 5.6 |
| Octyl | SC | 1.25 mM/kg | 10.2 |
| Octyl | IP | 4,8,15,25 | 8.6 |
| Octyl | IP | 4,8,15,25 | 6.8 |
| Octyl | IP | 4,8,15,25,50,100 | 8.1 |
| Oleyl | SC | 1.25 mM/kg | 7.2 |
| 9-Decenyl | SC | 1.25 mM/kg | 5.4 |

*Commercial analgesic
**O = oral; SC = subcutaneous; IP = intraperitoneal
***Multiple doses were 2 hours apart The data from Table II shows that octyl 4-hydroxyphenylacetamide has significant analgesic activity relative to the control composition and to the commercial analgesics, in particular aspirin and acetaminophen. This data would also indicate that decyl, nonyl and oleyl 4-hydroxyphenylacetamide have some analgesic activity relative to the control composition, and to aspirin and acetaminophen.

c. 3-Hydroxyphenylacetamides

The results from MHP testing of the 3-hydroxyphenylacetamides were as follows:

TABLE III

| Compound | Method** | Dosage (mg/kg)*** | Post-Drug Response (sec.) |
|---|---|---|---|
| Aspirin* | O | 360 | 6.0 |
| Acetaminophen* | O | 450 | 5.3 |
| Morphine Sulfate* | IP | 13 | 13.1 |
| Morphine Sulfate | IP | 25 | 17.4 |
| Control | SC or IP | — | 4.8–5.1 |
| Octyl | IP | 4,8,15,25,50,100 | 8.9 |

TABLE III-continued

| Compound | Method** | Dosage (mg/kg)*** | Post-Drug Response (sec.) |
|---|---|---|---|
| cis-9-Octadecenyl | SC | 0.68 mM/kg | 7.6 |

*Commercial analgesic.
**O = oral; SC = subcutaneous; IP = intraperitoneal.
***Multiple doses were 2 hours apart.

The data from Table III shows that octyl 3-hydroxyphenylacetamide has significant analgesic activity relative to the control composition and to the commercial analgesics, in particular aspirin and acetaminophen. This data would indicate that cis-9-octadecenyl 3-hydroxyphenylacetamide has some analgesic activity relative to the control composition, and to aspirin and acetaminophen.

B. Preventing or Reducing Depilatory Irritation

Groups of 8 male Sprague-Dawley rats weighing 90–115 grams were used for testing the effectiveness of several hydroxyphenylacetamides of the present invention in preventing or reducing depilatory irritation. The animals were clipped and depilated with Nair ®, a commercially available thioglycolate depilatory. The test compositions (2% of the particular hydroxyphenylacetamide in an isotonic saline solution containing 48% ethyl alcohol, 4% Tween 80) or a control composition (same as test composition but without the hydroxyphenylacetamide) were applied to one quadrant (Treated Area) of the depilated area once, 2 hours after depilation on first day; four times, 2 hours apart on second day; and three times, 2 hours apart on third day for a total of eight applications. The duration of each application was 2 hours. The remaining three quadrants of the depilated area were left untreated (Untreated Area). Oral ingestion was prevented by the use of "Elizabethan" collars. On the fourth day, the animals were depilated a second time and evaluated for irritation four hours later.

Irritation scores for each animal were determined by visual inspection using the following subjective evaluation scale:

| Score | Description of Irritation |
|---|---|
| 0 | No irritation |
| 0.5 | No scab formation, faint white scale |
| 1.0 | Scab formation (pale orange/orange) over less than 10% of area |
| 2.0 | Mild to moderate intensity scab formation (pale orange) over 10–33% of area |
| 3.0 | Mild to moderate intensity scab formation (pale orange) over 33–75% of area |
| 3.5 | Moderate intensity scab formation (pale orange, occasional deep orange/red) over 70–90% of area |
| 4.0 | Moderate to severe intensity scab formation (deep orange, occasional pale orange) over 90–100% of area |
| 5.0 | Severe intensity scab formation (deep orange/red) over 100% of area |

The irritation scores were totaled for each of the 8-animal groups, the maximum cumulative score being 40. A cumulative score of less than 8 indicated a minimal level of irritation; a score of 8–24 indicated a higher, but acceptable level of irritation; a score of above 24 indicated an unacceptable level of irritation. The results from this testing were as follows:

TABLE IV

| Composition* | Cumulative Score | |
|---|---|---|
| | Treated Area | Untreated Area |
| Control | 28–32 | 25–32 |
| 3,4-DPA | | |
| Nonyl | 33 | 15 |
| Octyl | 35 | 7 |
| 4-HPA | | |
| Decyl | 19.0 | 9.0 |
| Nonyl | 20.5 | 22.0 |
| Octyl | 3.5 | 8.0 |
| 3-HPA | | |
| Octyl | 2.0 | 2.5 |
| Octyl | 5.0 | 9.0 |
| cis-9-Octadecenyl | 28.0 | 18.5 |

*DPA = dihydroxyphenylacetamide; HPA = hydroxyphenylacetamide

The data from Table IV shows that decyl, nonyl and octyl 4-hydroxyphenylacetamide and octyl 3-hydroxyphenylacetamide were effective in preventing or reducing depilatory irritation; the octyl 3- and 4-hydroxyphenylacetamides were particularly effective.

What is claimed is:

1. A compound, or pharmaceutically acceptable salt thereof, having the formula:

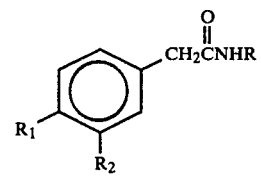

wherein R is a linear or branched $C_8$–$C_{10}$ alkyl group, a linear or branched $C_6$–$C_9$ alkynyl or aralkyl group, a linear or branched $C_{12}$–$C_{18}$ alkenyl group, or an unbranched or branched $C_6$–$C_{11}$ cycloalkyl or cycloalkenyl group; and wherein one of $R_1$ and $R_2$ is OH, the other being OH or H.

2. A pharmaceutically acceptable salt selected from the group consisting of sodium, potassium, calcium, magnesium, and ammonium salts of the compound according to claim 1.

3. A compound or salt thereof according to claim 1 wherein R is a $C_8$–$C_{10}$ alkyl group or a $C_{12}$–$C_{18}$ alkenyl group.

4. A compound or salt thereof according to claim 3 wherein R is n-octyl or n-octyl, and wherein $R_1$ and $R_2$ are both OH.

5. A compound or salt thereof according to claim 3 wherein R is n-octyl, n-nonyl or n-decyl, and wherein one of $R_1$ and $R_2$ is H.

6. A compound or salt thereof according to claim 5 wherein R is n-octyl.

7. A depilatory composition having reduced dermal irritation, which comprises:
 (a) a depilatory amount of a thioglycolate depilatory agent; and
 (b) a compound or salt thereof according to claim 5 in an amount effective to prevent or reduce the dermal irritation of the thioglycolate depilatory agent.

8. A composition according to claim 7 which further comprises a pharmaceutically acceptable carrier.

9. A method for preventing or reducing the dermal irritation caused by a thioglycolate depilatory agent, which comprises the step of applying to at least a portion of a depilated area the compound or salt thereof according to claim 5 in an amount effective to prevent or reduce irritation caused by treatment of the depilated area with a thioglycolate depilatory agent.

10. A pharmaceutical composition in unit dosage form having analgesic activity, which comprises a safe and effective amount of a compound, or pharmaceutically acceptable salt thereof, having the formula:

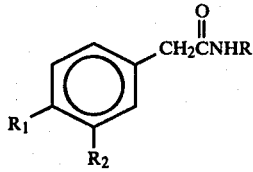

wherein R is a linear or branched $C_8$–$C_{10}$ alkyl group, a linear or branched $C_6$–$C_9$ alkynyl or aralkyl group, a linear or branched $C_{12}$–$C_{18}$ alkenyl group, or an unbranched or branched $C_6$–$C_{11}$ cycloalkyl or cycloalkenyl group; and wherein one of $R_1$ and $R_2$ is OH, the other being OH or H; and a pharmaceutically acceptable carrier.

11. A composition according to claim 10 comprising a pharmaceutically acceptable salt of said compound selected from the group consisting of sodium, potassium, calcium, magnesium, and ammonium salts.

12. A composition according to claim 10 wherein R is a $C_8$–$C_{10}$ alkyl group or a $C_{12}$–$C_{18}$ alkenyl group.

13. A composition according to claim 12 wherein R is n-octyl or n-nonyl, and wherein $R_1$ and $R_2$ are both OH.

14. A composition according to claim 12 wherein R is n-octyl, n-nonyl, n-decyl, cis-9-octadecenyl or oleyl, and wherein one of $R_1$ and $R_2$ are H.

15. A method for providing analgesia in humans and lower animals in need thereof which comprises the step of administering to the human or level animal a safe and effective amount of a compound, or pharmaceutically acceptable salt thereof, having the formula:

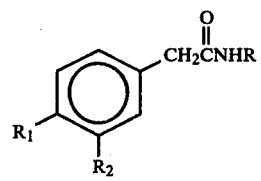

wherein R is a linear or branched $C_3$–$C_{11}$ alkyl, alkynyl or aralkyl group, a linear or branched $C_3$–$C_{22}$ alkenyl group, or an unbranched or branched $C_6$–$C_{11}$ cycloalkyl or cycloalkenyl group; and wherein one of $R_1$ and $R_2$ is OH, the other being OH or H.

16. A method according to claim 15 wherein the compound or salt thereof is administered topically.

17. A method according to claim 15 wherein the compound or salt thereof is administered parenterally.

18. A method according to claim 17 wherein the compound or salt thereof is administered intramuscularly.

19. A method according to claim 17 wherein the compound or salt thereof is administered intravenously.

20. A method according to claim 17 wherein the compound or salt thereof is administered subcutaneously.

21. A method according to claim 15 wherein the compound or salt thereof is administered in sequentially increasing doses.

22. A method according to claim 21 wherein the doses are separated by a period of at least about 2 hours.

23. A method according to claim 15 wherein R is a n-octyl or n-nonyl, and wherein $R_1$ and $R_2$ are both OH.

* * * * *